US008998897B2

(12) United States Patent
Binmoeller et al.

(10) Patent No.: US 8,998,897 B2
(45) Date of Patent: Apr. 7, 2015

(54) ABLATION CAP

(75) Inventors: Kenneth Binmoeller, San Francisco, CA (US); Richard W. Ducharme, Alexandria, PA (US); Tyler E. McLawhorn, Winston-Salem, NC (US); Vihar C. Surti, Winston-Salem, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 322 days.

(21) Appl. No.: 13/587,637

(22) Filed: Aug. 16, 2012

(65) Prior Publication Data

US 2013/0046300 A1  Feb. 21, 2013

Related U.S. Application Data

(60) Provisional application No. 61/525,385, filed on Aug. 19, 2011.

(51) Int. Cl.
*A61B 18/18* (2006.01)
*A61B 18/14* (2006.01)
(Continued)

(52) U.S. Cl.
CPC ... *A61B 18/1492* (2013.01); *A61B 2017/00296* (2013.01); *A61B 2018/00982* (2013.01); *A61B 2018/1475* (2013.01);
(Continued)

(58) Field of Classification Search
CPC ........... A61B 18/1492; A61B 1/00087; A61B 1/00089; A61B 1/00101; A61B 1/00131; A61B 2017/00296; A61B 2018/00982; A61B 2018/1475; A61B 2018/1495; A61B 2019/5483; A61B 2018/00577; A61B 2218/002
USPC ........................................... 606/41
See application file for complete search history.

(56) References Cited

U.S. PATENT DOCUMENTS 1,056,336 A  3/1913  Hurdman
4,074,718 A  2/1978  Morrison, Jr.
(Continued)

FOREIGN PATENT DOCUMENTS

JP    2009 183581 A    8/2009
WO   WO 98/22184       5/1998
(Continued)

OTHER PUBLICATIONS

International Search Report mailed Sep. 27, 2012 for International Application No. PCT/US2012/050899.
(Continued)

*Primary Examiner* — George Manuel
(74) *Attorney, Agent, or Firm* — Brinks Gilson & Lione (57) ABSTRACT

An ablation cap and a method of delivering energy to a tissue are provided. An ablation cap includes a tubular body having a proximal portion, a distal portion, a lumen extending therethrough. The ablation cap also includes a cover portion covering a portion of the tubular body, the covering portion having a region at least partially spaced apart from the tubular body and an electrode portion movably positionable relative to the cover portion. The electrode portion has a covered position where the electrode portion is positioned within the cover portion and an exposed position where the electrode portion is exposed relative to the cover portion. The proximal portion of the body is sized and shaped to fit on a distal end of an endoscope and the distal portion of the body extends distal to the distal end of the endoscope.

20 Claims, 8 Drawing Sheets

(51) Int. Cl.
   *A61B 17/00* (2006.01)
   *A61B 18/00* (2006.01)
   *A61B 19/00* (2006.01)
   *A61B 1/00* (2006.01)

(52) U.S. Cl.
   CPC  *A61B 2018/1495* (2013.01); *A61B 2019/5483* (2013.01); *A61B 1/00087* (2013.01); *A61B 1/00089* (2013.01); *A61B 1/00101* (2013.01); *A61B 1/00131* (2013.01)

(56) References Cited

U.S. PATENT DOCUMENTS

| | | | |
|---|---|---|---|
| 4,386,752 A | | 6/1983 | Pavlak et al. |
| 4,522,205 A | | 6/1985 | Taylor et al. |
| 4,532,924 A | | 8/1985 | Auth et al. |
| 4,706,667 A | | 11/1987 | Roos |
| 4,765,331 A | | 8/1988 | Petruzzi et al. |
| 4,823,791 A | | 4/1989 | D'Amelio et al. |
| 4,936,842 A | | 6/1990 | D'Amelio et al. |
| 5,100,402 A | | 3/1992 | Fan |
| 5,197,491 A | | 3/1993 | Anderson et al. |
| 5,254,121 A | | 10/1993 | Manevitz et al. |
| 5,443,470 A | | 8/1995 | Stern et al. |
| 5,454,809 A | | 10/1995 | Janssen |
| 5,494,483 A | | 2/1996 | Adair |
| 5,514,130 A | | 5/1996 | Baker |
| 5,562,703 A | | 10/1996 | Desai |
| 5,575,788 A | | 11/1996 | Baker et al. |
| 5,681,282 A | | 10/1997 | Eggers et al. |
| 5,683,385 A | | 11/1997 | Kortenbach et al. |
| 5,707,355 A | | 1/1998 | Zimmon |
| 5,718,702 A | | 2/1998 | Edwards |
| 5,743,870 A | | 4/1998 | Edwards |
| 5,766,168 A | | 6/1998 | Mantell |
| 5,836,906 A | | 11/1998 | Edwards |
| 5,906,587 A | | 5/1999 | Zimmon |
| 5,925,044 A | | 7/1999 | Hofmann et al. |
| 5,957,863 A | | 9/1999 | Koblish et al. |
| 5,993,446 A | | 11/1999 | Sutter |
| 5,994,717 A | | 11/1999 | Igarashi et al. |
| 6,009,877 A | | 1/2000 | Edwards |
| 6,027,499 A | | 2/2000 | Johnston et al. |
| 6,044,846 A | | 4/2000 | Edwards |
| 6,050,993 A | | 4/2000 | Tu et al. |
| 6,053,172 A | | 4/2000 | Hovda et al. |
| 6,056,744 A | | 5/2000 | Edwards |
| 6,059,719 A | | 5/2000 | Yamamoto et al. |
| 6,073,052 A | | 6/2000 | Zelickson et al. |
| 6,077,257 A | | 6/2000 | Edwards et al. |
| 6,086,585 A | | 7/2000 | Hovda et al. |
| 6,091,995 A | | 7/2000 | Ingle et al. |
| 6,112,123 A | | 8/2000 | Kelleher et al. |
| 6,135,999 A | * | 10/2000 | Fanton et al. ................. 606/45 |
| 6,149,647 A | | 11/2000 | Tu et al. |
| 6,156,032 A | | 12/2000 | Lennox |
| 6,190,381 B1 | | 2/2001 | Olsen et al. |
| 6,197,022 B1 | | 3/2001 | Baker |
| 6,210,409 B1 | | 4/2001 | Ellman et al. |
| 6,231,571 B1 | | 5/2001 | Ellman et al. |
| 6,245,067 B1 | | 6/2001 | Tu et al. |
| 6,258,084 B1 | | 7/2001 | Goldman et al. |
| 6,346,105 B1 | | 2/2002 | Tu et al. |
| 6,352,533 B1 | | 3/2002 | Ellman et al. |
| 6,355,032 B1 | | 3/2002 | Hovda et al. |
| 6,363,937 B1 | | 4/2002 | Hovda et al. |
| 6,394,949 B1 | * | 5/2002 | Crowley et al. ............... 600/127 |
| 6,402,744 B2 | | 6/2002 | Edwards et al. |
| 6,405,732 B1 | | 6/2002 | Edwards et al. |
| 6,419,673 B1 | | 7/2002 | Edwards et al. |
| 6,464,697 B1 | | 10/2002 | Edwards et al. |
| 6,494,881 B1 | | 12/2002 | Bales et al. |
| 6,535,764 B2 | | 3/2003 | Imran et al. |
| 6,535,768 B1 | | 3/2003 | Baker et al. |
| 6,544,261 B2 | | 4/2003 | Ellsberry et al. |
| 6,587,731 B1 | | 7/2003 | Ingle et al. |
| 6,589,238 B2 | | 7/2003 | Edwards et al. |
| 6,591,838 B2 | | 7/2003 | Durgin |
| 6,632,193 B1 | | 10/2003 | Davison et al. |
| 6,659,106 B1 | | 12/2003 | Hovda et al. |
| 6,669,687 B1 | | 12/2003 | Saadat |
| 6,685,713 B1 | | 2/2004 | Ahmed |
| 6,692,490 B1 | | 2/2004 | Edwards |
| 6,712,814 B2 | | 3/2004 | Edwards et al. |
| 6,740,082 B2 | | 5/2004 | Shadduck |
| 6,746,447 B2 | | 6/2004 | Davison et al. |
| 6,763,836 B2 | | 7/2004 | Tasto et al. |
| 6,846,312 B2 | | 1/2005 | Edwards et al. |
| 6,872,206 B2 | | 3/2005 | Edwards et al. |
| 6,918,906 B2 | | 7/2005 | Long |
| 6,932,812 B2 | | 8/2005 | Crowley et al. |
| 6,994,705 B2 | | 2/2006 | Nobis et al. |
| 7,022,105 B1 | | 4/2006 | Edwards |
| 7,025,768 B2 | | 4/2006 | Elliott |
| 7,097,644 B2 | | 8/2006 | Long |
| 7,137,981 B2 | | 11/2006 | Long |
| 7,232,438 B2 | | 6/2007 | Long |
| 7,252,665 B2 | | 8/2007 | Starkebaum et al. |
| 7,344,535 B2 | | 3/2008 | Stern et al. |
| 7,442,191 B2 | | 10/2008 | Hovda et al. |
| 7,530,979 B2 | | 5/2009 | Ganz et al. |
| 7,566,300 B2 | | 7/2009 | Devierre et al. |
| 7,648,500 B2 | | 1/2010 | Edwards et al. |
| 7,655,004 B2 | | 2/2010 | Long |
| 7,658,738 B2 | | 2/2010 | Nobis et al. |
| 7,662,151 B2 | | 2/2010 | Crompton, Jr. et al. |
| 7,678,069 B1 | | 3/2010 | Baker et al. |
| 7,691,101 B2 | | 4/2010 | Davison et al. |
| 7,703,459 B2 | | 4/2010 | Saadat et al. |
| 7,749,159 B2 | | 7/2010 | Crowley et al. |
| 7,758,087 B2 | | 7/2010 | Niven et al. |
| 2002/0177847 A1 | | 11/2002 | Long |
| 2002/0183739 A1 | | 12/2002 | Long |
| 2003/0181900 A1 | | 9/2003 | Long |
| 2003/0216727 A1 | * | 11/2003 | Long ............................. 606/41 |
| 2005/0080412 A1 | | 4/2005 | Ouchi |
| 2006/0167451 A1 | | 7/2006 | Cropper |
| 2006/0217698 A1 | | 9/2006 | Starkebaum et al. |
| 2007/0212926 A1 | | 9/2007 | Nakaura et al. |
| 2008/0103357 A1 | | 5/2008 | Zeiner et al. |
| 2008/0200912 A1 | | 8/2008 | Long |
| 2008/0242932 A1 | | 10/2008 | Carter |
| 2009/0221872 A1 | | 9/2009 | Liddle et al. |
| 2009/0270856 A1 | | 10/2009 | Saadat et al. |
| 2010/0087813 A1 | | 4/2010 | Long |
| 2010/0256632 A1 | | 10/2010 | Crowley et al. |

FOREIGN PATENT DOCUMENTS

| | | |
|---|---|---|
| WO | WO 99/35987 | 7/1999 |
| WO | WO 00/19926 | 4/2000 |
| WO | WO 01/68015 A1 | 9/2001 |
| WO | WO 2006/122279 A2 | 11/2006 |

OTHER PUBLICATIONS

Written Opinion mailed Sep. 27, 2012 for International Application No. PCT/US2012/050899.

R. Ackroyd et al., "Ablation treatment for Barrett oesophagus: what depth of tissue destruction is needed?," Clin Pathol, 1999;vol. 52, pp. 509-512.

C. P. Barham et al., "Photothermal laser ablation of Barrett's oesophagus: endoscopic and histological evidence of squamous re-epithelialisation," Gut, 1997, vol. 41, pp. 281-284.

R. M. Bremner et al., "Ultrasonic epithelial ablation of the lower esophagus without stricture formation," Surigical Endoscopy, 1998, vol. 12, pp. 342-347.

Gossner et al., "KTP laser destruction of dysplasia and early cancer in columnar-lined Barrett's esophagus," Gastointestinal Endoscopy, Jan. 1999, vol. 49, Issue 1. pp. 8-12.

(56) References Cited

OTHER PUBLICATIONS

H. Inoue et al., "Endoscopic mucosal resection with a cap-fitted panendoscope for esophagus, stomach, and colon mucosal lesions," Gastrointestinal Endoscopy, 1993 vol. 39, No. 1, pp. 58-62.

Johnston et al., "Endoscopic spray cryotherapy: a new technique for mucosal ablation in the esophagus," Gastrointestinal Endoscopy, Jul. 1999, vol. 50, pp. 86-92.

L. Laine, "Determination of the Optimal Technique for Bipolar Electrocoagulation Treatment," Gastroenterology, 1991, vol. 100, pp. 107-112.

B. Overholt, "Photodynamic therapy for Barrett's esophagus: follow-up in 100 patients," Gastrointestinal Endoscopy, 1999, vol. 49, No. 1, pp. 1-7.

Salo et al., "Treatment of Barrett's Esophagus by Endoscopic Laser Ablation and Antireflux Surgery," Annals of Surgery, vol. 227, No. 1, pp. 40-44, 1998.

T. V. Taylor et al., "Ablation of neoplasia by direct current," Br. J. Cancer, 1994, vol. 70, pp. 342-345.

J. van den Boogert, "Photodynamic Therapy for Esophageal Lesions: Selectivity Depends on Wavelength, Power, and Light Dose," The Society of Thoracic Surgeons, Nov. 1999, vol. 68, Issue 5, pp. 1763-1769.

International Search Report mailed Oct. 15, 2012 for International Application No. PCT/US2012/050516.

Written Opinion of the International Searching Authority mailed Oct. 15, 2012 for International Application No. PCT/US2012/050516.

* cited by examiner

ABLATION CAP

RELATED APPLICATIONS

This application claims the benefit of U.S. Provisional Application No. 61/525,385, filed Aug. 19, 2011, which is incorporated by reference herein in its entirety.

BACKGROUND

Millions of people suffer from progressive gastroesophageal reflux disease (GERD) which is characterized by frequent episodes of heartburn, typically on at least a daily basis. Without adequate treatment, GERD can cause erosion of the esophageal lining as the lower esophageal sphincter (LES), a segment of smooth muscle located at the junction of the stomach and the esophagus, gradually loses its ability to function as the barrier that prevents stomach acid reflux. Chronic GERD can also cause metaplasia to the inner lining of the esophagus where the normal squamous mucosa changes to columnar mucosa, also known as Barrett's esophagus. Barrett's esophagus can progress to esophageal cancer if left untreated.

Endoscopic treatment of Barrett's esophagus includes endoscopic mucosal resection (EMR). One method of performing EMR involves ablation of the mucosal surface by heating the surface until the surface layer is no longer viable. The dead tissue is then removed.

Treatment devices for performing EMR have been developed using bipolar ablation technology that includes positioning a probe against the target tissue and delivering energy to the tissue to ablate the tissue in contact with the probe. The probes may be provided on an inflatable balloon. The balloon must be inflated to a predetermined size to achieve contact with the diseased tissue for delivery of the appropriate amount of energy from the bipolar ablation device to ablate the diseased tissue. In order to determine the correct size and balloon pressure to achieve adequate ablation, a sizing balloon must first be introduced into the esophagus. The sizing balloon adds an extra step to the procedure when a balloon inflated probe is used for tissue ablation. In addition, the inflated balloon is delivered over a wire guide and alongside the endoscope. The inflated balloon is positioned in front of the endoscope viewing window, preventing direct visualization of the target tissue and potentially leading to ablation of healthy tissue or incomplete ablation of diseased tissue.

What is needed in the art is an ablation treatment device that is simple to use, that is coupled to the endoscope, that minimizes the number of steps and time required for a treatment procedure and that provides treatment under direct endoscopic visualization.

BRIEF SUMMARY

Accordingly, it is an object of the present invention to provide a device and a method having features that resolve or improve on one or more of the above-described drawbacks.

In one aspect, an ablation cap is provided. The ablation cap includes a tubular body having a proximal portion, a distal portion, a lumen extending therethrough. The ablation cap also includes a cover portion covering a portion of the tubular body, the covering portion having a region at least partially spaced apart from the tubular body and an electrode portion movably positionable relative to the cover portion. The electrode portion has a covered position where the electrode portion is positioned within the cover portion and an exposed position where the electrode portion is exposed relative to the cover portion. The electrode portion includes a plurality of electrodes. The proximal portion of the body is sized and shaped to fit on a distal end of an endoscope and the distal portion of the body extends distal to the distal end of the endoscope.

In another aspect, an ablation cap is provided. The ablation cap includes a tubular body having a proximal portion, a distal portion, a lumen extending therethrough. The ablation cap also includes a cover portion covering a portion of the tubular body, the covering portion having a region at least partially spaced apart from the tubular body and an electrode portion movably positionable relative to the cover portion. The electrode portion has a covered position where the electrode portion is positioned within the cover portion and an exposed position where the electrode portion is exposed relative to the cover portion. The proximal portion of the body is sized and shaped to fit on a distal end of an endoscope and the distal portion of the body extends distal to the distal end of the endoscope and the electrode portion is movably positionable into and out of view through the endoscope.

In another aspect, a method of delivering energy to a tissue site within a patient's lumen using the ablation cap is provided. The method includes positioning the ablation cap within a patient's lumen, the ablation cap positioned on a distal end of an endoscope. The ablation cap includes a tubular body having a proximal portion, a distal portion, a lumen extending therethrough, a cover portion covering a portion of the tubular body, the covering portion having a region at least partially spaced apart from the tubular body and an electrode portion movably positionable relative to the cover portion, the electrode portion includes a plurality of electrodes. The method further includes moving the electrode portion relative to the cover portion to an exposed position to expose the electrode portion, contacting the tissue with the electrode portion, supplying energy to the plurality of electrodes from an energy source and ablating the tissue.

DETAILED DESCRIPTION

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the ablation cap to a patient. Hence the term "distal" means the portion of the ablation cap that is farthest from the physician and the term "proximal" means the portion of the ablation cap that is nearest to the physician.

Figures 1, 2A:
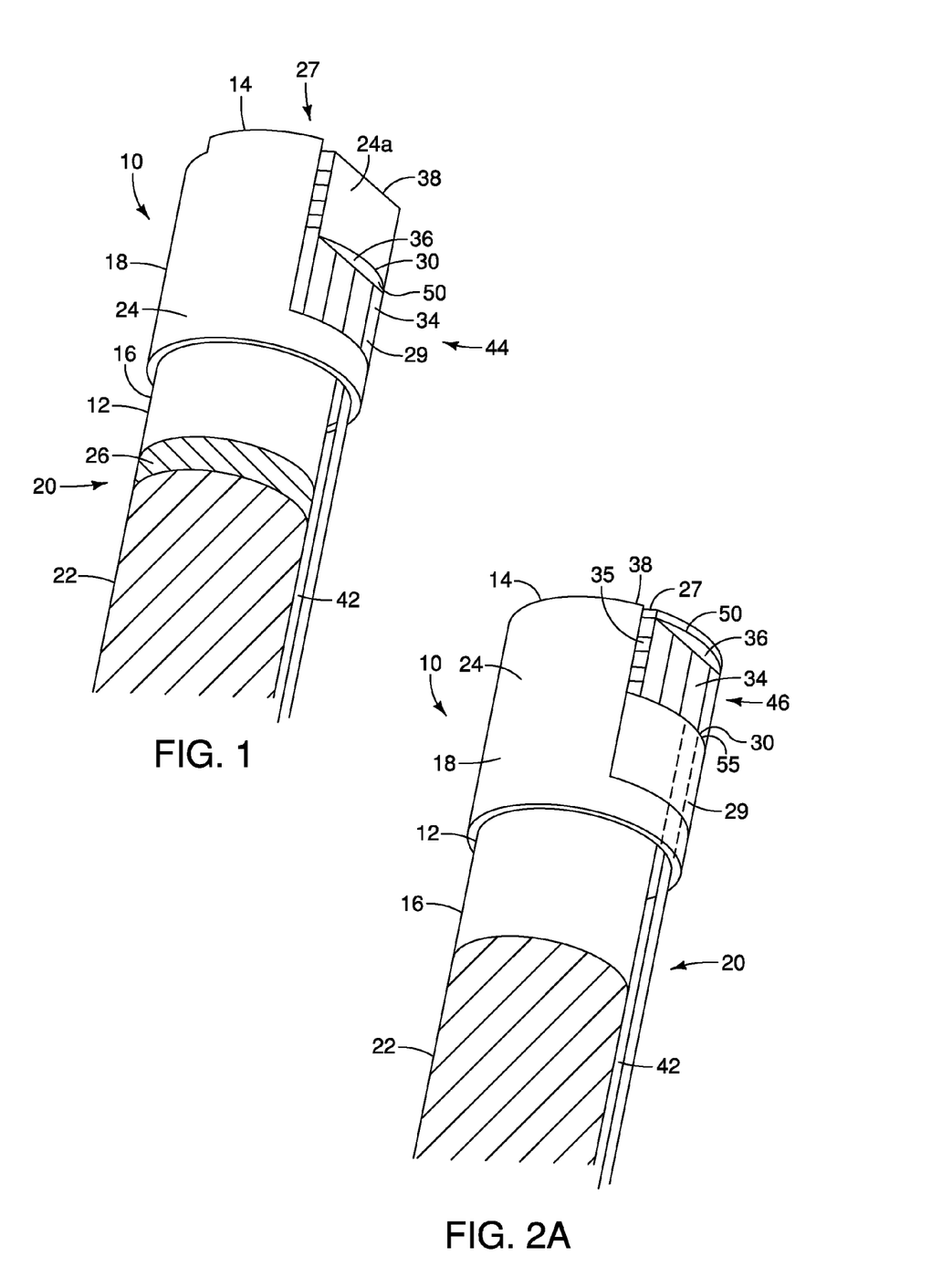
FIG. 1 is a top view of an ablation cap with an electrode portion in a covered position on a distal end of an endoscope in accordance with an embodiment of the present invention.
FIG. 2A is a perspective view of the ablation cap shown in FIG. 1 with the electrode portion in an exposed position.
Figure 2B:
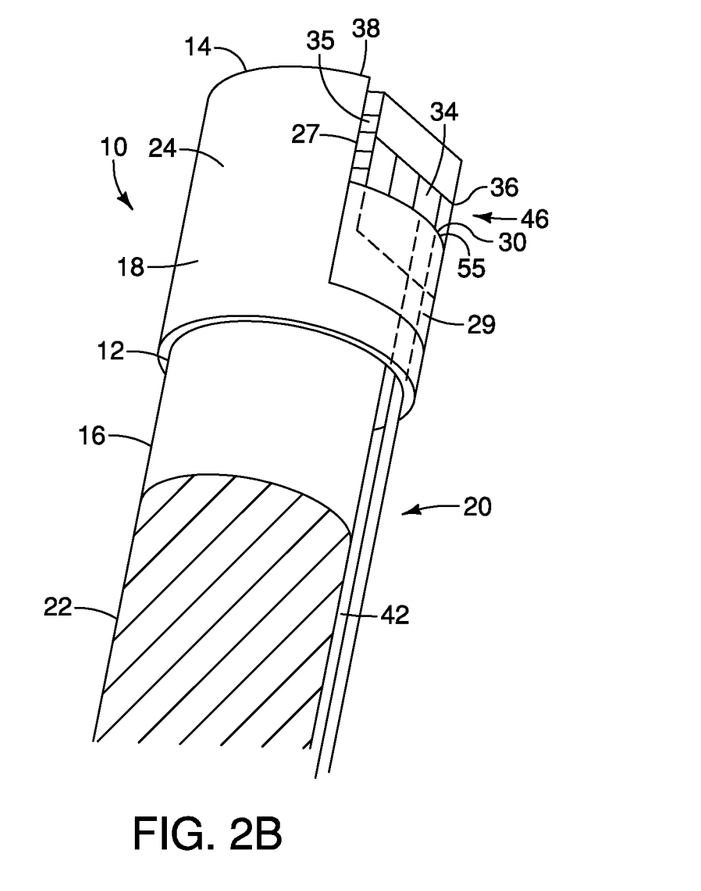
FIG. 2B is a perspective view of the ablation cap shown in FIG. 1 with the electrode portion in an exposed position with the electrode portion distally extended less than 100%.
Figure 11A:
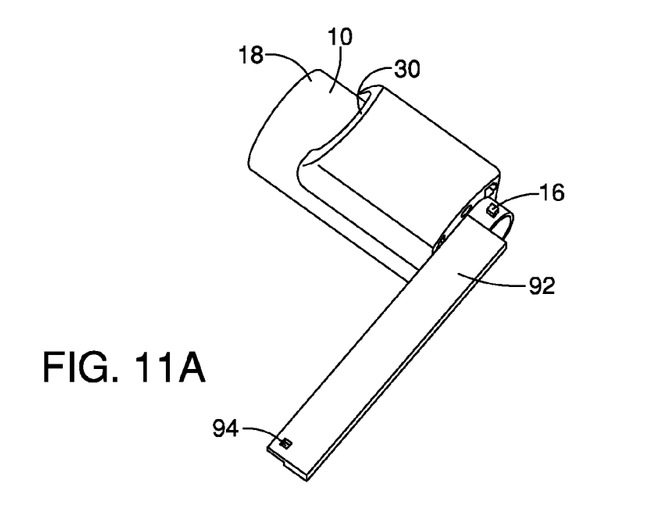
FIGS. 11A-11C illustrate a band for securing an ablation cap to an endoscope in accordance with an embodiment of the present invention.
Figure 11B:
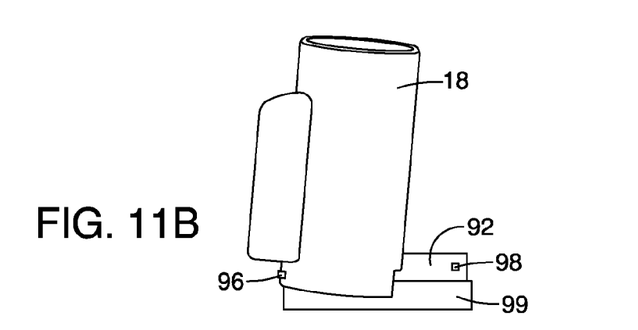
Figure 11C:
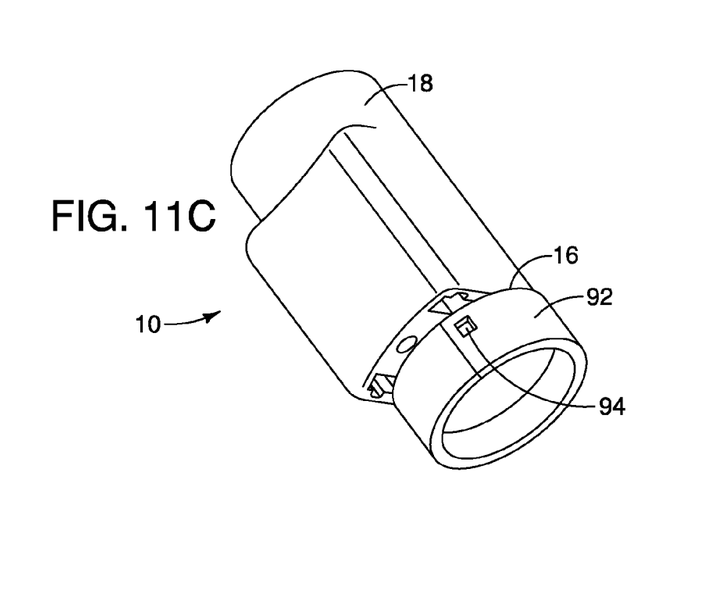

FIGS. 1, 2A and 2B illustrate an embodiment of an ablation cap 10 in accordance with the present invention. As shown in FIGS. 1, 2A and 2B, the ablation cap 10 includes a tubular body 12 having a lumen 14 formed therein. The ablation cap 10 includes a proximal portion 16 and a distal portion 18. As shown in FIGS. 1, 2A and 2B, the proximal portion 16 of the cap 10 is sized to fit on a distal end 20 of an endoscope 22. In some embodiments, the proximal portion 16 of the ablation cap 10 may include a flexible portion 26 that is connected to the tubular body 12 and that fits over the distal end 20 of the endoscope 22 to secure the cap 10 to the endoscope 22. In some embodiments, the proximal portion 16 may be made of a hard material that is sized and shaped to fit over the distal end 20 of the endoscope 22 by friction fit. In some embodiments, the cap 10 may be secured to the endoscope 22 using a band 92 shown in FIGS. 11A-11C that surrounds the proximal portion 16 of the cap 10 and a portion of the distal end 20 of the endoscope 22. The cap 10 may be positioned over the distal end of the endoscope (not shown) and the band 92 may be pulled around the proximal portion 16 of the cap 10. As shown in FIGS. 11A-11C, the band 92 may include one or more openings 94 that are secured over one or more corresponding notches 96 on the proximal portion of the cap 10. The band 92 may include a recessed portion 98 to fit against the proximal portion 16 of the cap 10 and a second portion 99 to fit against the endoscope 22 so that the cap 10 is secured to the endoscope 22 (See FIG. 11B). The band 92 may be tape, leather, elastomeric material or other material suitable for securing the cap 10 to the endoscope 22.

The distal portion 18 of the ablation cap 10 may extend beyond the distal end 20 of the endoscope 22. The distal portion 18 may be cylindrical. In some embodiments, the distal portion 18 may be formed from a material having sufficient transparency so that the operator using an optical port of the endoscope 22 may observe a portion of the tissue to be treated by viewing the tissue through a wall 24 of the distal portion 18 of the ablation cap 10. The distal portion 18 may also include a portion that is formed from a material for magnifying the tissue under observation. The cap 10 may further include a cover portion 29 that includes a recess 30 formed as part of the ablation cap 10. The cover portion 29 may be integrally formed with the cap 10 or provided as a separate portion and connected to the cap 10. The cover portion 29 is at least partially spaced apart from the tubular body to form the recess 30. The recess 30 may be sized and shaped to hold an extendable electrode portion 34 within the recess 30 in a covered position 44 as shown in FIG. 1. The electrode portion 34 is slidably positionable within the recess 30 of the cover portion 29. In some embodiments, the electrode portion 34 may be positioned entirely within the recess 30 of the cover portion 29 in the covered position 44 so that electrodes positioned on the electrode portion 34 are completely covered. As shown in FIGS. 2A and 2B, the electrode portion 34 may be extended distally from the recess 30 so that at least a portion of a surface 35 of the electrode portion is exposed and can contact the tissue to be treated. A portion 24a of the wall 24 is positioned behind the electrode portion 34 when the electrode portion 34 is an exposed position 46 and may be used to support the electrode portion 34 when the electrode portion 34 is pressed against the tissue to be treated. In some embodiments, a distal end 36 of the electrode portion 34 does not extend beyond a distal end 38 of the distal portion 18 of the cap 10.

In some embodiments, the distal portion 18 of the cap 10 may also include a plurality of demarcations 27 to indicate the where the electrode portion 34 is in relation to the cap 10 and how far the electrode portion 34 has been advanced distally. As shown in FIG. 2A, the distal end 36 of the electrode portion 34 is extended to the maximum extension that is not beyond the distal end 38 of the distal portion 18 of the cap 10 and is positioned adjacent to the most distal demarcation 27. In some embodiments, the distal end 36 of the electrode portion 34 is extended less than the maximum extension as shown in FIG. 2B. By way of non-limiting example, the distal end 36 may be extended Less than 100% or about 20%, 40%, 60% and 80% of the maximum extension. Other extension distances are also possible. In some embodiments, the electrode portion 34 may be colored to facilitate viewing the electrode portion 34 as it is advanced distally and to determine the amount that the electrode portion 34 has been extended. For example, the electrode portion 34 may be black or blue or any color that may be seen through an endoscope to help viewing the position of the electrode portion 34. In some embodiments, the cap 10 may include a stop 55 to stop the electrode portion 34 at the maximum extension and to prevent the electrode portion from extending too far out of the cap 10.

In some embodiments, at least a portion of the electrode portion 34 may be viewable through the endoscope. The electrode portion 34 may move into and out of the view of the endoscope, for example when the electrode portion 34 has been extended a certain percent relative to the cap 10, the electrode portion 34 may be viewed through the endoscope. By way of non-limiting example, the electrode portion 34 may be viewed when 10%, 20%, 30%, 40%, 50%, 60%, 70%, 80%, 90%, 100% or other amount has been extended distally. The electrode portion 34 may also be energized when the electrode portion 34 is extended distally less than 100%.

As shown in FIGS. 1 and 2, the electrode portion 34 may be connected to a drive catheter 42 that extends proximally from the electrode portion 34 to a proximal control handle (not shown). The drive catheter 42 is distally movable to extend the electrode portion 34 from the recess 30 of the cover portion 29 and proximally movable to re-position the electrode portion 34 within the recess 30. Typically, the electrode portion 34 is positioned within the recess 30 of the cover portion 29 when the ablation cap 10 is being delivered to a treatment site or being repositioned within a patient's lumen for additional treatment at one or more additional sites. Positioning of the electrode portion 34 within the recess 30 also helps to prevent accidental energy delivery, for example to healthy tissue. The electrode portion 34 is at least partially distally extended from the recess 30 of the cover portion 29 for treatment at a site and energy is delivered to the tissue to ablate the diseased tissue as described in more detail below.

In some embodiments, the electrode portion 34 may include a beveled portion 48 on a distal end 50 of the electrode portion 34 as shown in FIG. 1. Movement of the drive catheter 42 proximally and distally may be used to facilitate the scraping of tissue to remove coagulum. In addition, movement of the endoscope 22 proximally and distally may also be used to facilitate the scraping. The beveled portion 48 may be used to scrape treated tissue to help remove the tissue after treatment.

Figure 3:
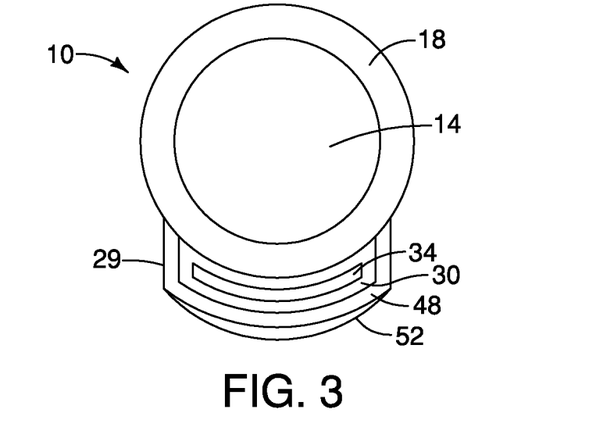
FIG. 3 is an end view of an embodiment of an ablation cap.
Figure 4:
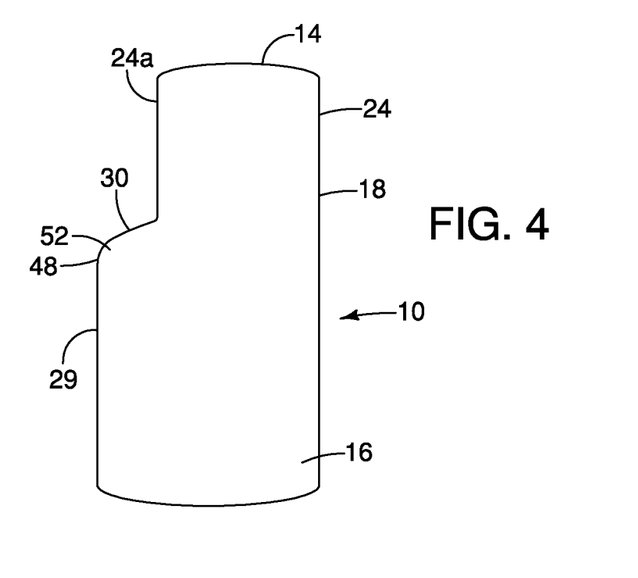
FIG. 4 is a side view of an embodiment of an ablation cap.

An end view of an embodiment of the ablation cap 10 is shown in FIG. 3. The lumen 14 extends through the ablation cap 10 between the proximal portion 16 and the distal portion 18. The electrode portion 34 is shown within the recess 30 of the cover portion 29. In the embodiment shown, a beveled portion 48 is positioned on a distal edge 52 of the recess 30. A side view of an embodiment of the cap 10 is shown in FIG. 4. The beveled portion 48 may be used to help prevent tissue entrapment within the recess 30.

Figure 5:
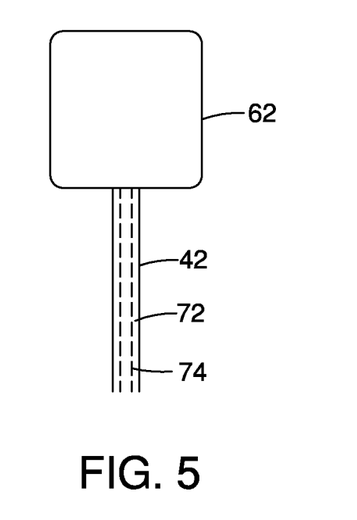
FIG. 5 is a partial view of an embodiment of a support member of the ablation cap.
Figure 6:
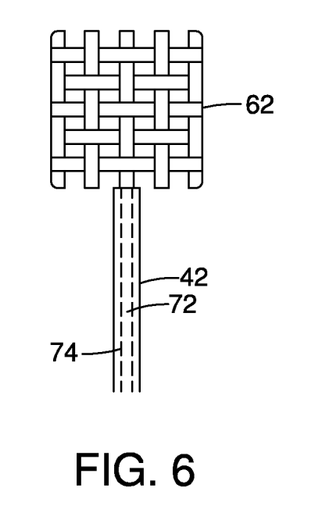
FIG. 6 is a partial view of an embodiment of a support member of the ablation cap.

In some embodiments, the electrode portion 34 may include a support member 62 upon which one or more electrodes 64 are positioned. FIGS. 5 and 6 illustrate exemplary support members 62. As shown in FIG. 5, the support member 62 may be a solid material, such as a plastic material. As shown in FIG. 6, the support member 62, may be a mesh. When the solid material or the mesh is formed of a metallic material, a layer of insulation may be provided between the support member 62 and the electrodes 64. The support member 62 may be moved proximally and distally with the drive catheter 42. The electrodes 64 may be secured to the support member 62 by any method known to one skilled in the art. By way of non-limiting example, the electrodes may be secured by gluing, bonding, taping, an adhesive backing on the electrodes, crimping, manufacturing the electrodes directly on to the body and the like.

Electrical wires 72 may extend through a lumen 74 of the drive catheter 42 as shown in FIGS. 5 and 6 and connect to the electrodes 64 to supply the energy for ablation. Alternatively, the electrical wires 72 may extend through a lumen of the endoscope 22. The electrodes 64 may be seen in FIGS. 7 and 8. The electrodes 64 may be provided separately from the support member 62 and in some embodiments may also form the support member 62 without providing a separate support member.

Figure 7:
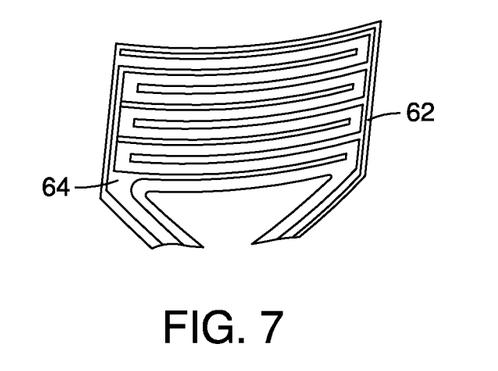
FIG. 7 illustrates an embodiment of an electrode of the ablation cap.
Figure 8:
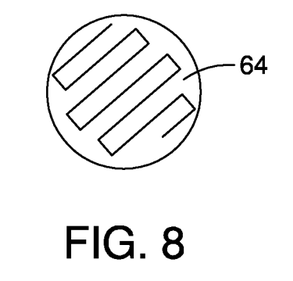
FIG. 8 illustrates an embodiment of an electrode of the ablation cap.

As shown In FIGS. 7 and 8, the electrodes 64 may include positive electrodes 64 and negative electrodes 64 in a bipolar device and when provided as a bipolar device the electrodes 64 are provided in pairs, one positive and one negative electrode per pair. The electrodes 64 may also be provided as a monopolar device having a single electrode 64 or a plurality of electrodes 64 with a grounding pad or an impedance circuit additionally provided (not shown). The electrodes 64 may be provided in any pattern on the support member 62. The electrodes 64 may cover the entire support member 64 or a portion thereof. By way of non-limiting example, a space 62 between the positive electrode portion 64 and the negative electrode portion 64 may between about 0.1 mm to about 5 mm. In some embodiments, the energy may be delivered to the tissue for a period of time from about 0.1 second to about 10 seconds. In some embodiments, the amount of energy delivered to the tissue may be from about 10 watts to about 60 watts. Other spacing distances between electrodes, length of time, and energy delivery are also possible and depend on the target tissue, the depth of the lesion, the type of energy, the length of application of the energy to the tissue and the spacing of the electrodes.

The electrodes 64 are operably connected to an energy source (not shown). In some embodiments, the energy source may be a radio frequency source. However, other types of energy sources may also be used to provide energy to the electrodes. By way of non-limiting example, additional possible energy sources may include microwave, ultraviolet, cryogenic and laser energies.

Figure 9:
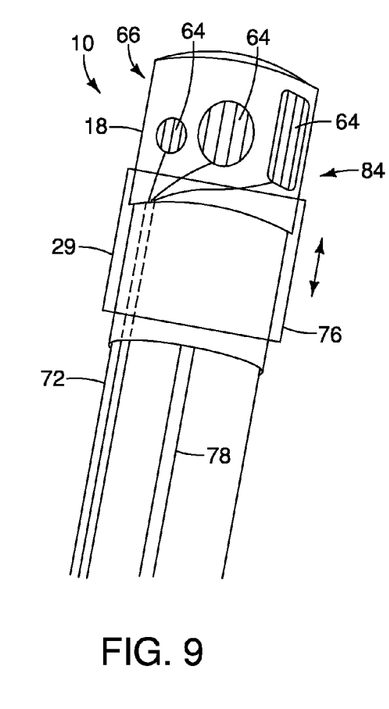
FIG. 9 is a perspective view of an ablation cap with an electrode portion in an exposed position on a distal end of an endoscope in accordance with an embodiment of the present invention.

In some embodiments, the electrodes 64 may be provided on the distal portion 18 of the cap 10 as shown in FIG. 9. The cap 10 may include a plurality of electrodes 64 in separate areas 66 on the cap 10. The separate areas 66 of electrodes 64 may be separately energizable for treatment of the tissues. The areas 66 may include bipolar or monopolar electrodes 64 as described above. The areas 66 may be provided with a plurality of different sizes and patterns to provide treatment for different sized sites. The areas 66 may extend around a circumference of the cap 10 or just a portion of the circumference. The electrodes 64 may also extend entirely around the ablation cap 10 in a single area 66 and may be energized in sections or in the entirety depending on the treatment site. By way of non-limiting example, spacing 62 between the positive electrode 64 and the negative electrode 64 may between about 0.1 mm to about 5 mm. In some embodiments, the energy may be delivered to the tissue for a period of time from about 0.1 second to about 10 seconds. In some embodiments, the amount of energy delivered to the tissue may be from about 10 watts to about 60 watts. Other spacing distances between electrodes, length of time, and energy delivery are also possible and depend on the target tissue, the depth of the lesion, the type of energy, the length of application of the energy to the tissue and the spacing of the electrodes.

Figure 10:
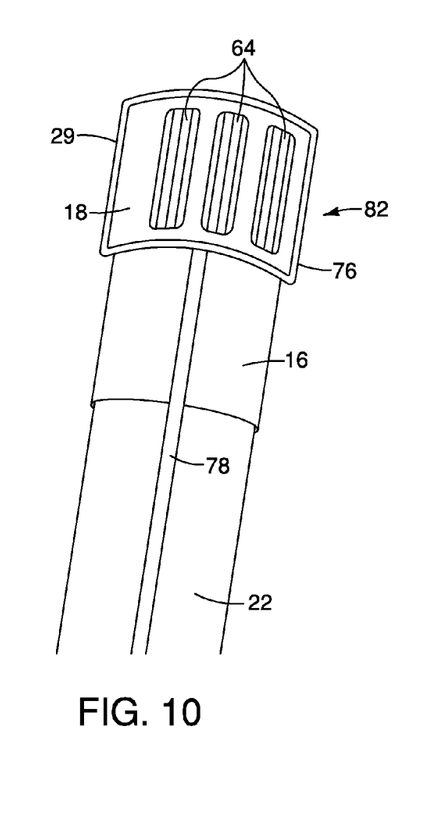
FIG. 10 is a perspective with of the ablation cap shown in FIG. 9 with the electrode portion in a covered position.

In the embodiments having the electrodes 64 provided on the distal portion 18 of the cap 10, the ablation cap 10 may further include the cover portion 29 comprising a sleeve portion 76 as shown in FIGS. 9 and 10. The sleeve portion 76 is movable distally to cover the electrodes 64 in a covered position 82 as shown in FIG. 10. The sleeve portion 76 is movable proximally to expose the electrodes 64 in an exposed position 84 as shown in FIG. 9 for treatment of the tissue. The sleeve portion 76 may be moved using a drive catheter 78. Similar to the electrode portion 34 described above, the sleeve portion 76 covers the electrodes 64 during positioning of the ablation cap 10 at the treatment site or for repositioning the ablation cap 10 within the patient's lumen so that the electrodes 64 are entirely covered. The sleeve portion 76 may be pulled proximally for exposure of the electrodes 64 and treatment of the tissue site when the electrodes 64 are in position at the treatment site.

In some embodiments, the ablation cap may be made primarily of a substantially transparent or translucent polymer such as polytetrafluorothylene (PTFE). Additional possible materials include, but are not limited to the following, polyethylene ether ketone (PEEK), fluorinated ethylene propylene (FEP), perfluoroalkoxy polymer resin (PFA), polyamide, polyurethane, high density or low density polyethylene, and nylon. In some embodiments, the ablation cap may be formed from a lubricious material such as PTFE and the like for easy slidability within the patient's lumen for delivery to the treatment site. In some embodiments, the ablation cap or a portion thereof may be formed from magnifying or other image enhancing materials. The ablation cap or a portion thereof may also be coated or impregnated with other compounds and materials to achieve the desired properties. Exemplary coatings or additives include, but are not limited to, parylene, glass fillers, silicone hydrogel polymers and hydrophilic coatings.

Figure 12A:
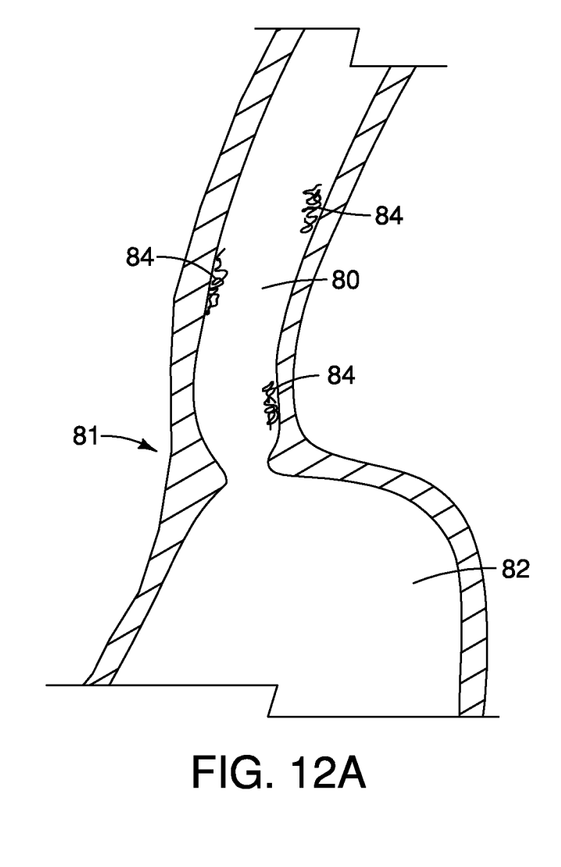
FIGS. 12A-12C illustrate operation of the ablation cap.
Figure 12B:
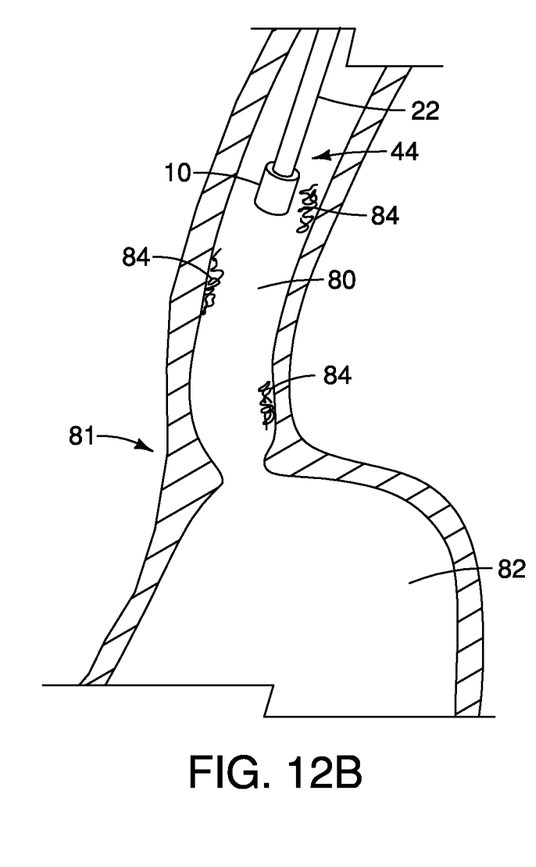
Figure 12C:
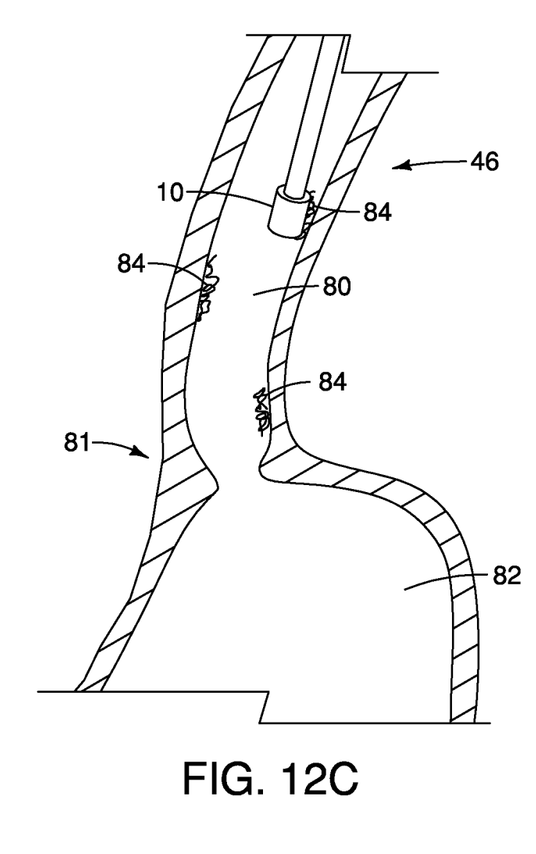

Operation of the ablation cap using the ablation cap 10 as a non-limiting example will be explained with reference to FIGS. 12A-12C. FIG. 12A illustrates a patient's esophagus 80, lower esophageal sphincter (LES) 81 and stomach 82. Areas of diseased tissue 84 within the esophagus 80 are also shown. The diseased tissue 84 may be columnar mucosa (Barrett's esophagus) that is to be ablated using the ablation cap 10. FIG. 12B illustrates the ablation cap 10 positioned on the distal end 20 of the endoscope 22 and the cap 10 and the endoscope 22 being inserted into the patient's esophagus 80. The ablation cap 10 is positioned in the esophagus 80 near the portion of the diseased tissue 84 to be treated. The insertion of the ablation cap 10 may be monitored using the viewing port of the endoscope to help position the cap 10 at the diseased tissue. As shown in FIG. 12B, the ablation cap 10 is positioned near the diseased tissue 84. While the ablation cap 10 is being positioned, the electrode portion 34 is in the covered position 44. As shown in FIG. 12C, the diseased tissue 84 is in contact with the electrode portion 34 in the exposed position 46 so that the electrodes 64 and in contact with the diseased tissue 84 and can deliver energy to the diseased tissue 84 to ablate the diseased tissue 84. A power source (not shown) is activated for a sufficient time to ablate the diseased tissue 84. The ablation cap 10 may be repositioned near another portion of diseased tissue 84 for treatment and the steps repeated as many times as needed. The electrode portion 34 may be extended and viewed through the viewing port as the electrode portion 34 extends distally. While the procedure has been described with reference to the ablation of diseased tissue in the esophagus using the ablation cap 10, the location of the treatment is not limited to the esophagus. By way of non-limiting example, portions of the stomach, or the gastrointestinal tract may also be treated using the ablation cap 10.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. An ablation cap comprising:
   a tubular body having a proximal portion, a distal portion, a lumen extending therethrough;
   a cover portion covering a portion of the tubular body, the portion having a region at least partially spaced apart from the tubular body;
   an electrode portion movably positionable relative to the cover portion, the electrode portion having a covered position wherein the electrode portion is positioned within the cover portion; and an exposed position wherein the electrode portion is distally movable relative to the cover portion and is exposed relative to the cover portion, the electrode portion comprising a plurality of electrodes; and
   a stop to stop the electrode portion at a maximum extension in the exposed position;
   wherein the proximal portion of the body is sized and shaped to fit on a distal end of an endoscope and the distal portion of the body extends distal to the distal end of the endoscope.

2. The ablation cap of claim 1, wherein the cover portion is fixed in position on the proximal portion of the tubular body and includes a recess formed between the cover portion and the tubular body.

3. The ablation cap of claim 2, further comprising a drive catheter operably connected to the electrode portion for moving the electrode portion to the covered and exposed positions.

4. The ablation cap of claim 1, wherein the cover portion is movable relative to the tubular body.

5. The ablation cap of claim 1, wherein the electrode portion is distally extendable so that a distal end of the electrode portion does not extend beyond a distal end of the distal portion of the body.

6. The ablation cap of claim 1, wherein the plurality of electrodes are bipolar electrodes.

7. The ablation cap of claim 1, wherein the tubular body comprises a transparent material, a translucent material or a magnifying material.

8. The ablation cap of claim 1, wherein the electrode portion comprises a beveled edge extending axially away from the cap to scrape tissue.

9. The ablation cap of claim 1, wherein the cap comprises a plurality of demarcations to indicate the position of the electrode portion relative to the cover.

10. The ablation cap of claim 1, wherein the electrode portion further comprises separate areas, each separate area comprising an electrode, each electrode being separately energizable.

11. The ablation cap of claim 1, wherein the electrode portion, in the covered position, is positioned entirely within the cover portion.

12. The ablation cap of claim 1, wherein the distal portion of the tubular body is cylindrical so that the electrode portion is at least partially supported by the tubular body in the exposed position.

13. An ablation cap comprising:
    a tubular body having a proximal portion, a distal portion, a lumen extending therethrough;
    a cover portion covering a portion of the tubular body, the covering portion having a region at least partially spaced apart from the tubular body;
    an electrode portion movably positionable relative to the cover portion, the electrode portion having a covered position wherein the electrode portion is positioned within the cover portion; and an exposed position wherein the electrode portion is distally movable relative to the cover portion and is exposed relative to the cover portion; and
    a stop to stop the electrode portion at a maximum extension in the exposed position;
    wherein the proximal portion of the body is sized and shaped to fit on a distal end of an endoscope and the distal portion of the body extends distal to the distal end of the endoscope; and
    wherein the electrode portion is movably positionable into and out of view through the endoscope.

14. The ablation cap of claim 13, wherein the cap further comprises a plurality of demarcations to indicate the position of the electrode portion relative to the cover.

15. The ablation cap of claim 13, wherein the electrode portion is distally extendable and energizable when the electrode portion is extended less than 100%.

16. The ablation cap of claim 13, wherein a wire connects the electrode portion to an energy source and the wire extends external to the endoscope.

17. A method of delivering energy to a tissue site within a patient's lumen, the method comprising:
    positioning an ablation cap within a patient's lumen, the ablation cap positioned on a distal end of an endoscope, the ablation cap comprising:
    a tubular body having a proximal portion, a distal portion, a lumen extending therethrough;

a cover portion covering a portion of the tubular body, the covering portion having a region at least partially spaced apart from the tubular body; and an electrode portion movably positionable relative to the cover portion, the electrode portion comprising a plurality of electrodes;

moving the electrode portion relative to the cover portion to an exposed position to expose the electrode portion, controlling the amount of extension and providing a stop to stop the electrode portion at a maximum extension;

contacting the tissue with the electrode portion;

supplying energy to the plurality of electrodes from an energy source; and ablating the tissue.

18. The method of claim 17, further comprising moving the electrode portion relative to the cover portion to return the electrode portion to a covered position and repositioning the ablation cap at a second tissue site to be treated.

19. The method of claim 17, further comprising scraping the tissue to remove a coagulum.

20. The method of claim 17, comprising viewing the tissue through a magnifying portion of the tubular body.

\* \* \* \* \*

UNITED STATES PATENT AND TRADEMARK OFFICE
CERTIFICATE OF CORRECTION

PATENT NO. : 8,998,897 B2  
APPLICATION NO. : 13/587637  
DATED : April 7, 2015  
INVENTOR(S) : Kenneth Binmoeller et al.

It is certified that error appears in the above-identified patent and that said Letters Patent is hereby corrected as shown below:

In the Claims

In column 7, claim 1, line 44, before "portion having a region" insert --cover--.

Signed and Sealed this
Seventeenth Day of May, 2016

Michelle K. Lee
*Director of the United States Patent and Trademark Office*